US009314207B2

(12) United States Patent
Marterstock

(10) Patent No.: US 9,314,207 B2
(45) Date of Patent: Apr. 19, 2016

(54) DEVICE AND METHOD FOR AUTHORIZING THE OPERATION OF A MEDICAL APPARATUS USING A PORTABLE IDENTIFICATION DEVICE CARRIED BY AN OPERATOR

(71) Applicant: Fresenius Medical Care Deutschland GmbH, Bad Homburg (DE)

(72) Inventor: Stefan Konrad Marterstock, Eussenheim-Hundsbach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 52 days.

(21) Appl. No.: 14/092,007

(22) Filed: Nov. 27, 2013

(65) Prior Publication Data
US 2014/0148104 A1 May 29, 2014

Related U.S. Application Data

(60) Provisional application No. 61/730,546, filed on Nov. 28, 2012.

(30) Foreign Application Priority Data

Nov. 28, 2012 (DE) .......................... 10 2012 111 523

(51) Int. Cl.
*H04B 7/00* (2006.01)
*A61B 5/00* (2006.01)
(Continued)

(52) U.S. Cl.
CPC ............... *A61B 5/681* (2013.01); *A61B 5/4866* (2013.01); *A61B 19/44* (2013.01); *A61M 1/14* (2013.01);
(Continued)

(58) Field of Classification Search
CPC ............ A61B 19/44; A61B 2019/448; A61B 5/4866; A61B 5/681; A61M 1/14; A61M 2205/276; A61M 2205/3561; A61M 2205/3584; A61M 2205/3592; A61M 2205/52; A61M 2205/60; A61M 2205/6054
See application file for complete search history.

(56) References Cited

U.S. PATENT DOCUMENTS 6,676,621 B1 1/2004 Menninger
2001/0052858 A1 12/2001 Vincent et al.
(Continued)

FOREIGN PATENT DOCUMENTS

DE 19849787 2/2000
DE 102010041338 3/2012
(Continued)

OTHER PUBLICATIONS

Wireless lock, In: Wikipedia, the free encyclopedia, URL:http://en.wikipedia.org/w/index,php?title=Wireless_lock.
(Continued)

*Primary Examiner* — Golam Sorowar
(74) *Attorney, Agent, or Firm* — Jacobson Holman, PLLC.

(57) ABSTRACT

Treatment system for a patient, preferably for performing a dialysis treatment, including a medical apparatus, preferably a dialysis apparatus, having a communication device which is configured to emit a wireless interrogation signal and receive a wireless identification signal, and an identification device which can be carried by an operator to identify the operator. The identification device is preferably embodied as a watch and is configured to send a wireless identification signal to the medical apparatus to confirm the identity of the operator and that the operator is authorized to operate the medical apparatus to which the signal has been sent.

16 Claims, 2 Drawing Sheets

(51) Int. Cl.
*A61M 1/14* (2006.01)
*H04W 12/06* (2009.01)
*G06F 19/00* (2011.01)
*H04L 29/08* (2006.01)
*A61B 19/00* (2006.01)

(52) U.S. Cl.
CPC .......... *G06F 19/323* (2013.01); *G06F 19/3406* (2013.01); *G06F 19/3468* (2013.01); *H04L 67/12* (2013.01); *H04W 12/06* (2013.01); *A61B 2019/448* (2013.01); *A61M 2205/276* (2013.01); *A61M 2205/3561* (2013.01); *A61M 2205/3584* (2013.01); *A61M 2205/3592* (2013.01); *A61M 2205/52* (2013.01); *A61M 2205/60* (2013.01); *A61M 2205/6054* (2013.01)

(56) References Cited

U.S. PATENT DOCUMENTS

| | | | |
|---|---|---|---|
| 2004/0172222 | A1 | 9/2004 | Simpson et al. |
| 2005/0234381 | A1 | 10/2005 | Niemetz et al. |
| 2007/0055321 | A1* | 3/2007 | Gordon et al. .................. 607/55 |
| 2007/0201025 | A1 | 8/2007 | Greenwald |
| 2009/0094033 | A1* | 4/2009 | Mozer et al. .................. 704/251 |
| 2009/0146822 | A1* | 6/2009 | Soliman .................... 340/573.1 |
| 2009/0222671 | A1 | 9/2009 | Burbank et al. |
| 2010/0085160 | A1* | 4/2010 | Fu ............................... 340/10.1 |
| 2010/0318578 | A1* | 12/2010 | Treu et al. ..................... 707/802 |
| 2011/0093294 | A1* | 4/2011 | Elahi et al. ....................... 705/3 |
| 2011/0105854 | A1* | 5/2011 | Kiani et al. .................... 600/300 |
| 2012/0075061 | A1 | 3/2012 | Barnes |
| 2012/0117057 | A1* | 5/2012 | Adimatyam et al. ......... 707/723 |
| 2012/0218111 | A1* | 8/2012 | Batchelder et al. ........ 340/573.1 |
| 2012/0294378 | A1* | 11/2012 | Ackley et al. ................. 375/259 |

FOREIGN PATENT DOCUMENTS

| | | |
|---|---|---|
| EP | 1576972 | 9/2005 |
| WO | WO 2007/061368 | 5/2007 |
| WO | WO 2010/044088 | 4/2010 |

OTHER PUBLICATIONS

Bluetooth low energy. In: Wikipedia, the free encyclopedia, URL:http://en.wikipedia.org/w/index.php?title=Bluetooth_low_energy.

Bluetooth.com;Phones:2012 URL: http://www.bluetooth.com/Pages/Phones.aspx.

Abdelhameed, Application of Cell-phonein Laptop Security, Journal of Applied Sciences, vol. 5, No. 2, 2005, pp. 215-219.

Business Wire: Seiko Instruments Inc. and Ensure Technologies Demonstrate First Interactive Bluetooth Wristwatch Using Hands-Free Computer Security. In: The Free Library, 2001, S. 1-3, http://www.thefreelibrary.com/Seiko.

Gartner, Bluetooth Gets Some Bite;Wired;2001. S. 1 URL:http://www.wired.com/science/discoveries/news/2001/03/42620.

Naveed et al. An Authentication Framework for Nomadic Users, In: NODES 09; Nordic workshop and doctoral symposium on Dependability and Security, 2009, S. 33-42.

* cited by examiner ized under the designation "5008".

DEVICE AND METHOD FOR AUTHORIZING THE OPERATION OF A MEDICAL APPARATUS USING A PORTABLE IDENTIFICATION DEVICE CARRIED BY AN OPERATOR

TECHNICAL FIELD

The invention relates to a medical apparatus for treating a patient, an identification device for an operator of a medical apparatus, a treatment system for a patient comprising a medical apparatus and an identification device, and a method for checking an authorization of an operator of a medical apparatus. The said medical apparatus and/or treatment system are preferably used to perform a dialysis treatment of a patient.

STATE OF THE ART

"Medical apparatuses" are understood here in particular as apparatuses for conveying, treating and/or distributing fluids and/or gases, wherein fluid is transported via a fluid line between a patient and a fluid treatment component and/or a fluid source.

"Medical apparatuses" are also understood in particular as fluid treatment apparatuses such as for example blood treatment apparatuses, in which a fluid of a patient is led via a fluid line to a fluid treatment component, treated by the fluid treatment component, and returned to the patient via the fluid line, which can be divided into an arterial branch and a venous branch. Examples of such blood treatment apparatuses are in particular hemodialysis apparatuses.

Such a blood treatment apparatus is the subject-matter of the applicant's DE 198 49 787 C1, the content of which is hereby incorporated in full in the disclosure content of the present application.

Dialysis is a method for purifying the blood of patients with acute or chronic renal insufficiency. In this, there is a basic distinction between methods with an extracorporeal blood circulation, such as hemodialysis, hemofiltration or hemodiafiltration, and peritoneal dialysis, which does not have an extracorporeal blood circulation.

In hemodialysis, blood is sent in an extracorporeal circulation through the blood chamber of a dialyzer. The blood chamber is separated by a semipermeable membrane from a dialysis fluid chamber, through which a dialysis fluid containing the blood electrolyte in a certain concentration flows. The substance concentration of the blood electrolyte in the dialysis fluid corresponds to the concentration in the blood of a healthy person. During the treatment, the patient's blood and the dialysis fluid are passed on both sides of the semipermeable membrane, usually in countercurrent, at a predetermined flow rate. Substances that must be eliminated from the urine diffuse through the membrane from the blood chamber into the chamber for dialysis fluid, while at the same time electrolytes present in the blood and in the dialysis fluid diffuse from the chamber having the higher concentration to the chamber having the lower concentration. If a pressure gradient is applied from the blood side to the dialysate side of the dialysis membrane, for example by a pump downstream of the dialysis filter on the dialysate side which draws dialysate from the dialysate circulation, water passes from the patient's blood via the dialysis membrane into the dialysate circulation. This ultrafiltration process brings about a desired removal of water from the patient's blood.

In hemofiltration, ultrafiltrate is withdrawn from the patient's blood by the application of a transmembrane pressure in the dialyzer, without dialysis fluid being passed across the opposite side of the dialyzer membrane from the patient's blood. In addition, a sterile and pyrogen-free substitution solution can be added to the patient's blood. According to whether this substitution solution is added upstream or downstream of the dialyzer, this is termed predilution or postdilution. In hemofiltration, the exchange of substances is by convection.

Hemodiafiltration combines the methods of hemodialysis and hemofiltration. There is both a diffusive exchange of substances between the patient's blood and the dialysis fluid via the semipermeable membrane of a dialyzer, and a filtering out of plasma water through a pressure gradient at the membrane of the dialyzer.

The methods of hemodialysis, hemofiltration and hemodiafiltration, which are collectively referred to hereinafter as "hemodialysis", are usually carried out using automatic hemodialysis apparatuses, such as that marketed by the applicant under the designation "5008".

Plasmapheresis is a blood treatment method in which the patient's blood is separated into the blood plasma and its corpuscular components (cells). The separated blood plasma is purified or replaced with a substitution solution, and the purified blood plasma or the substitution solution is returned to the patient.

In peritoneal dialysis, a patient's abdominal cavity is filled with a dialysis fluid through a catheter passed through the abdominal wall. This dialysis fluid has a concentration gradient with respect to the body's own fluids. The toxins present in the body enter the abdominal cavity through the peritoneum, which functions as a membrane. After a few hours, the spent dialysis fluid inside the patient's abdominal cavity is replaced. Water can pass by processes of osmosis from the patient's blood via the peritoneum into the dialysis fluid, and is thereby removed from the patient.

The method of peritoneal dialysis is usually carried out using automatic peritoneal dialysis apparatuses, such as for example the apparatus marketed by the applicant under the designation "sleep.safe".

Dialysis apparatuses, as examples of complex medical apparatuses, have an extensive set of functions. In order to control these functions, medical apparatuses such as dialysis apparatuses are equipped with at least one control device. This can be realized as a CPU (central processing unit) or microcontroller, both of which are programmed by software programs to carry out the functions. Such apparatuses are commonly operated via touch screen displays. Such a touch screen display combines an input and an output device in a single surface, by providing a touch-sensitive surface which can detect an operator's inputs.

Possible embodiments provide spatial separation of the input and output devices, for example using a conventional display, realized for example as a CRT (cathode ray tube) monitor, LCD (liquid crystal display), plasma display or OLED (organic light emitting device) display, as the output device, and, spatially separate from this, a touch pad providing a touch-sensitive surface which can detect an operator's inputs as an input device.

The treatment of patients in dialysis facilities requires that the applicable dialysis machines are set up and adjusted by specially trained operating personnel. Since a typical dialysis station may contain different designs of dialysis machines, it can occur that certain dialysis nurses are not trained to operate all dialysis apparatuses, and accordingly only those personnel who have received the appropriate training may perform a certain operation of a machine, particularly an operation with critical parameters. Hitherto the only way of controlling this has been to forbid the relevant dialysis personnel from operating the applicable dialysis apparatuses.

In addition, it is necessary to prevent intentional or unintentional manipulation of the dialysis apparatuses during a dialysis procedure by the patients themselves, visitors or other persons.

The only means to ensure this hitherto has been surveillance of the relevant areas.

SUMMARY OF THE INVENTION

An object of the present invention is to improve the operational safety of medical apparatuses, and correspondingly increase patient safety.

This object is achieved by a treatment system for a patient, preferably for performing a dialysis treatment, comprising a medical apparatus, preferably a dialysis apparatus, having a communication device which is configured to emit a wireless interrogation signal and receive a wireless identification signal, and an identification device which can be carried by an operator to identify the operator in which the identification device is configured to send a wireless identification signal to the medical apparatus.

Accordingly, a treatment system for a patient is proposed, preferably for performing a dialysis treatment, comprising a medical apparatus, preferably a dialysis apparatus, having a communication device which is configured to emit a wireless interrogation signal and receive a wireless identification signal, and an identification device which can be carried by an operator to identify said operator, wherein the identification device is configured to send a wireless identification signal to the medical apparatus.

Provision of the identification device, which serves to send an identification signal wirelessly to the medical apparatus, makes it possible to transmit identification data from a particular operator and/or from operating personnel to the medical apparatus to be operated in each case. Accordingly, in the medical apparatus, on the basis of the signal that is received, changes to the operating parameters can then either be enabled or blocked.

In this manner it becomes possible to require each authorized operator to carry a corresponding identification device such that the particular operator can operate only those medical apparatuses for which he or she is certified and/or authorized. In this manner it is possible to prevent the operation of a medical apparatus by an operator who does not have the applicable qualification, or has not received instruction in that model of apparatus. In this manner it is further possible to prevent the patient himself, or visitors, or other persons who are present in the applicable medical station, in particular a dialysis station, from making changes to the parameters of the medical apparatus, either intentionally or unintentionally.

It further becomes possible to log the changes made by each qualified operator, and use this to attribute a particular parameter change to a specific operator. In this manner it is feasible, using a log which, for example, is kept in the applicable medical apparatus, to document the treatment of each patient in full, recording not only the time and extent of changes to parameters, but also which operator carried out each parameter change.

The device for identifying an operator is preferably realized in a manner that enables an operator to carry it with him or her without difficulty. It can for example be in a form similar to that of a wristwatch, or else for example in the form of a device similar to a pager, which can be attached to clothing or a belt, or instead in the form of suitable mobile phones, smartphones or portable computers, which are in each case provided in individualized form for a particular operator.

It is particularly preferable for the communication device to be configured to send an individual identification signal for each operator. Accordingly, each device for identification of an operator can be individualized for the respective operator. For this purpose the applicable operator can be required, for example at the beginning of his or her shift, to register with the device, for example by entering a username and a corresponding password or a corresponding PIN code (PIN is an abbreviation for "personal identification number"). The combination of username and PIN activates the corresponding identification device, so that the operator who carries the device can perform the applicable changes to the parameters of those medical apparatuses which he or she is qualified and authorized to operate.

It is particularly preferable for the device to have an autonomous energy supply, for example by means of a suitable battery or accumulator. This enables particularly flexible use of the device, and makes it comfortable for the operator to wear or carry.

In one alternative, the device can be configured to transmit a wireless identification signal, for example using a passive RFID chip (RFID is an abbreviation for "radio-frequency identification"), which can give information about its identity when requested to do so by the medical apparatus.

In a particularly preferred variant, the device further comprises an alerting device, which is configured to inform and/or alert an operator concerning a particular critical state of a medical apparatus. For this purpose it is envisaged that the medical apparatus itself transmits an appropriate alarm signal to the identification device that is carried by the applicable operator, and in this manner also alerts this operator. For this purpose provision can also be made to issue such an alert message to all operators in the vicinity. In this, it is particularly preferable if at the same time the location of the medical apparatus that issues the alarm is shown on the identification device, along with an indication of the reason for the alarm.

In order to individualize each identification device, it is possible to provide both software-based individualization features and other machine-readable individual codes, which can be transmitted from the identification device on request by the medical apparatus, in order to identify the operator to the medical apparatus. The individual codes can be for example fixed IP addresses or MAC addresses which are specific to the identification device.

A treatment system accordingly comprises a medical apparatus, preferably a dialysis apparatus, and an identification device, which is configured to be able to communicate wirelessly with the medical apparatus. In response to a request from the medical apparatus, which is preferably sent at short intervals, for example every 0.5 seconds, an identification device in the immediate vicinity of the medical apparatus is prompted to send a suitable identification signal to the medical apparatus.

The identification device can for example be in the form of a pager, a mobile phone or a mobile computer, in particular a tablet PC, and is particularly preferably in the form of a device which can be worn or carried directly on the person, such as for example in the form of a wristwatch, which simultaneously performs the identification function.

In both the medical apparatus and the identification device, suitable communication devices are provided which enable the medical apparatus to communicate with the identification device. This communication preferably takes place wirelessly, and preferably via electromagnetic waves, using for example WLAN, Bluetooth, or other wireless radio transmission protocols. Communication can also be provided via an infra-red connection, wherein communication via an infra-red connection functions reliably only if there is a direct line-of-sight connection between the medical apparatus and the identification device. Thus the provision of an infra-red connection can be envisaged in addition to a wireless radio connection, in order thereby to provide a redundant communication channel and enable even more accurate identification of an operator.

In normal operation, the medical apparatus and the identification device communicate with each other with a low transmission power. In normal operation it is also only necessary to identify the operator in the immediate vicinity of the apparatus unambiguously, and accordingly enable or block the applicable operating elements on the medical apparatus. In particular, the medical apparatus is here configured such that an alteration of certain parameters, in particular an alteration of critical parameters, can be performed on the medical apparatus only if correct identification of the respective operator has taken place. In this manner it is possible to prevent the alteration of the applicable parameters by unqualified or unauthorized operators, and the occurrence of accidental or unintended alterations to parameters.

When the operator wishes to operate the medical apparatus, he or she will be located in the immediate vicinity of the medical apparatus, in order to be able to operate it.

The medical apparatus can constantly request the identity of the operator, for example by emitting a suitable request code word at a certain interval, for example every 0.5 seconds. Alternatively however, a request can also be initiated only when particular operating elements of the medical apparatus are operated. In this case, the operation of the applicable operating elements can either be triggered via the actual operation of the operating elements, for example buttons, touch screens or control knobs, or else as a result of the applicable operating elements being additionally configured to be touch-sensitive. Accordingly, a request from the communication device in the medical apparatus can be initiated, for example by means of a capacitive touch sensor, as soon as the operating element is touched by the operator, thereby determining whether the operation is in fact performed by an identifiable and authorized operator, or instead is performed accidentally or by an unqualified operator. In one variant, the request concerning qualification or authorization of the operator can also be initiated via the control device of the medical apparatus if an operator inputs a command to change a parameter.

In a further preferred variant, the communication device which is provided in the medical apparatus is configured such that, as well as the periodic requests to the identification devices in the vicinity, and/or such requests initiated in response to an attempted operating action, it also has a second mode of operation, in which an alarm signal is sent with a significantly higher transmission power to the surrounding identification devices. For this purpose the transmission power of the communication device in the medical apparatus is greatly increased, in order to reach as many as possible of the medical personnel who are not normally in the immediate vicinity of the medical apparatus. Here it is possible to transmit, alongside the actual alarm message, also the location of the medical apparatus that sends the alarm and the reason for the alarm, so that the medical personnel can adjust themselves in advance to the expected situation. For example, a dialysis nurse can be notified by the sending of a suitable alert of, for example, a serious medical incident, for example a patient's circulatory malfunction, so that this nurse can summon a doctor immediately, without having to go first to the patient in order to investigate the situation before alerting a doctor. In this manner, valuable time can also be saved if the urgency of the particular alarm and/or the particular reason for the alarm is also transmitted.

The above-mentioned object is further achieved by a medical apparatus, preferably a dialysis apparatus, for a treatment system having a communication device and an identification device. Accordingly, the medical apparatus is preferably a dialysis apparatus and is provided for the treatment system described above. In accordance with the invention, a communication device is configured to emit a wireless interrogation signal and receive a wireless identification signal from an identification device carried by an operator. In this manner, the advantages of identification of an operator that are described above can be achieved.

The above-mentioned object is also further achieved by a portable identification device, for a medical apparatus for a treatment system including a communication device as described above. Accordingly, the portable identification device serves to identify an operator of a medical apparatus in the treatment system described above. In accordance with the invention, a communication device is provided which is configured to receive a wireless interrogation signal and send a wireless identification signal to a medical apparatus in response to the interrogation signal. In this manner, the advantages of identification of an operator that are described above can be achieved.

A portable identification device having a communication device configured to emit periodically a wireless identification signal, for identifying an operator of a medical apparatus for a treatment system described above is further proposed. In accordance with the invention, a communication device is provided which is configured to emit periodically a wireless identification signal, preferably with a low transmission power. In this manner, the identification of an operator can be compelled by a medical apparatus, for example in order to identify maintenance staff.

By means of a method for emitting an identification signal from an identification device, which is carried by and identifies an operator, for a treatment system, an operator of a medical apparatus of the treatment system described above can be identified. Accordingly, the steps are provided of: wireless emission of an interrogation signal by a communication device of the medical apparatus to at least one identification device carried by an operator and identifying said operator; reception in the communication device of the medical apparatus of a wireless identification signal sent in response to the received interrogation signal; and identification of the operator based on the received identification signal.

The object is also achieved by a method for emitting an identification signal from an identification device carried by an operator and identifying said operator for a treatment system as described above. Accordingly, the steps are provided of: reception of a wireless interrogation signal emitted from a medical apparatus in a communication device of the identification device; and wireless emission of an identification signal in response to the received interrogation signal by the communication device of the identification device.

A method is further proposed for emitting an identification signal from an identification device carried by an operator and identifying said operator, with the step of periodic emission of a wireless identification signal for reception in the communication device of a medical apparatus. In this manner, the identification of an operator can be compelled by a medical apparatus, for example in order to identify maintenance staff.

By means of a computer program product, the above-mentioned method can be carried out in a medical apparatus of a treatment system as described above. In this, the computer program product is preferably executed in a control device of the medical apparatus, in order to achieve the identification of an operator.

By means of a computer program product, the above-mentioned method can also be carried out in an identification device of a treatment system as described above. This computer program product is also particularly suitable for carrying out the method of emitting an identification signal on an existing mobile phone, smartphone and/or portable computer, in particular a tablet PC.

In general, the medical apparatus and a computer in accordance with the teaching of the present invention are provided with specific programming which suitably controls the operation of the medical apparatus, or the display of data from the medical apparatus or a treatment carried out with the medical apparatus, and/or the use of sensors for monitoring and controlling the medical apparatus or a treatment carried out with it, as well as carrying out the methods described.

These specific instances of programming are computer programs, and can be loaded directly into an internal memory store of the computer and/or the medical apparatus, and can comprise software code sections which execute the methods described when the programs run on the computer or the medical apparatus. The computer programs can be available on data media as computer program products which comprise computer-readable program means. These data media can be inserted into a computer and comprise, alongside physical memory storage such as diskettes, CD-ROMs, memory cards, USB drives or DVDs, also storage within networks, such as the internet, to which the operator can have access.

BRIEF DESCRIPTION OF THE FIGURES

Further preferred embodiments and aspects of the present invention are more fully explained by the description below of the figures. The figures show.

DETAILED DESCRIPTION OF EXAMPLES OF PREFERRED EMBODIMENTS

Examples of preferred embodiments are described below with the aid of the figures. In the figures, elements which are identical or similar, or have identical effects, are designated with identical reference signs, and repeated description of these elements is in part dispensed with, in order to avoid redundancy.

Figure 1:
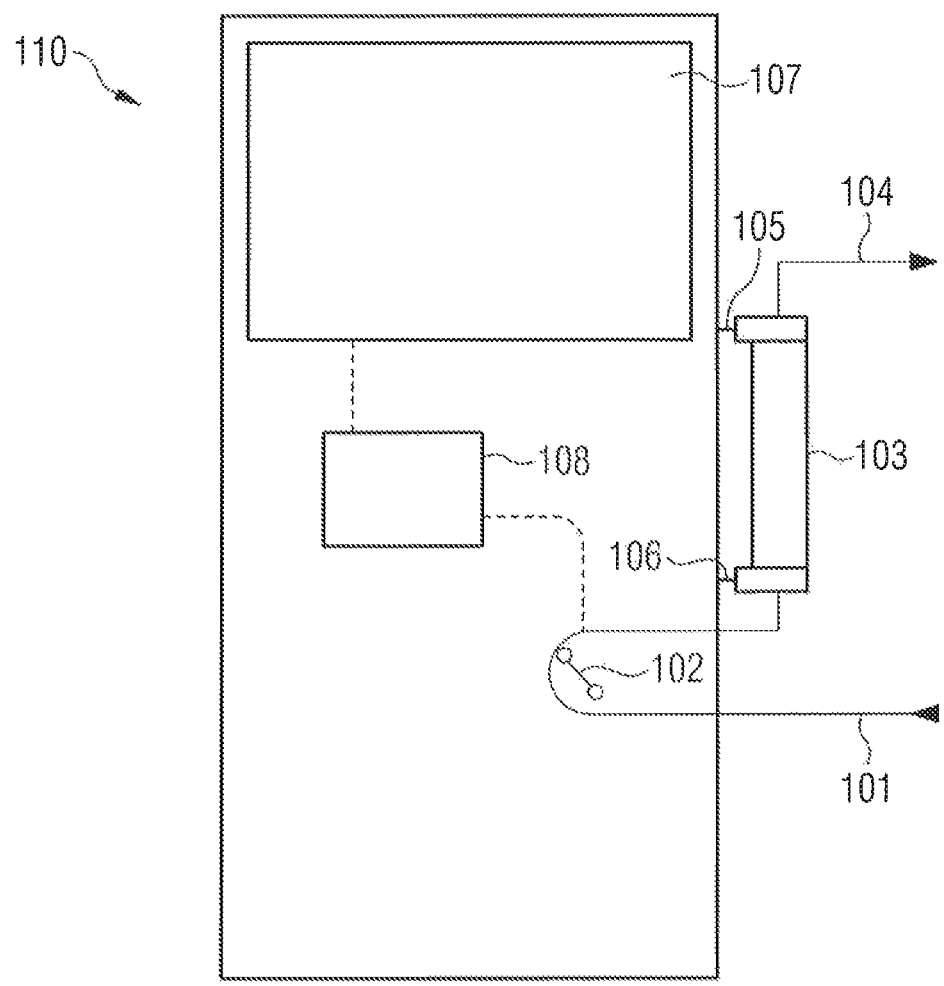
FIG. 1 a conventional medical apparatus, in the form of a hemodialysis apparatus.

FIG. 1 shows schematically an embodiment of a conventional medical apparatus 110 as a hemodialysis apparatus or a dialysis machine with a touch screen display 107. The medical apparatus 110 has an extensive set of functions, and is provided with a control device 108 to control these functions. This control device 108 can be realized as a CPU (central processing unit) or microcontroller, which is configured, for example by means of software programs running on it, to control or execute the functions. In FIG. 1 a connection of the control device 108 to a blood pump 102 is shown schematically, by means of which the control device 108 can access the blood pump 102. The touch screen display 107 serves, among other uses, to access the control device 108 such that an operator can enter and/or select particular instructions, parameters or sequence programs of the control device 108. The medical apparatus 110 shows, as an indication, parts of an extracorporeal blood circulation with an arterial blood line 101, which conveys the blood from a patient (not shown). The blood pump 102 pumps the blood through a dialysis filter 103, which is equipped with a semipermeable membrane that separates the extracorporeal blood circulation semipermeably from a dialysate circulation. The treated blood is returned to the patient via the venous line 104. Via the dialysate lines 105 and 106, dialysate is pumped through the dialysis filter 103, where there is a diffusive exchange of substances with the patient's blood via the semipermeable membrane of the dialysis filter 103. If in addition a pressure gradient is applied from the blood side of the dialysis filter to the dialysate side, plasma water is pressed out of the patient's blood into the dialysate. The pressed-out plasma water is also known as ultrafiltrate. In this manner, water can be removed from the patient's blood. The dialysate is produced in the hemodialysis apparatus 110, and discarded after use.

Figure 2:
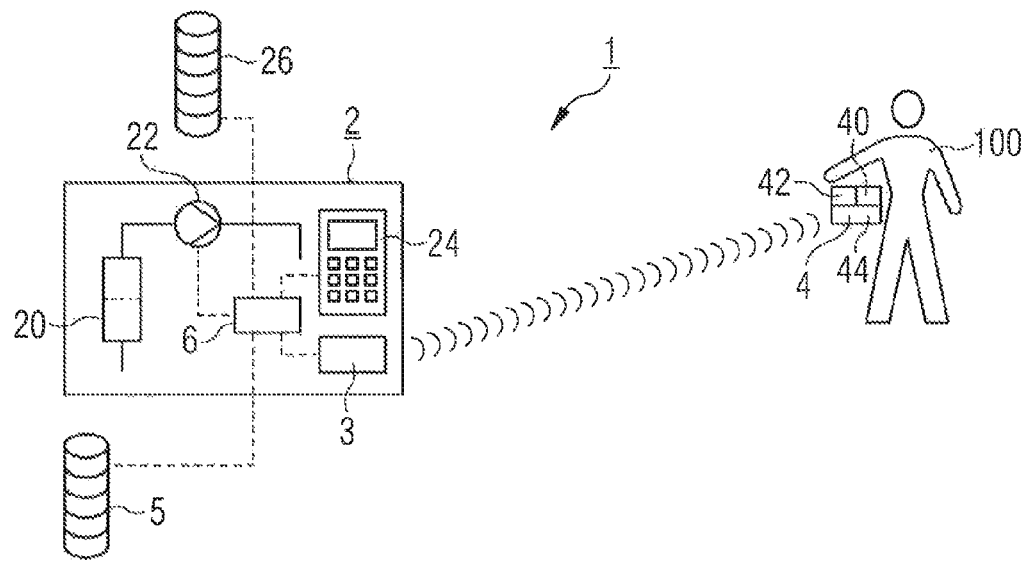
FIG. 2 a schematic diagram of a treatment system with a medical apparatus and an identification device.

FIG. 2 shows schematically a treatment system 1, which comprises a medical apparatus 2 in the form of a schematically indicated dialysis apparatus with a filter 20, a peristaltic pump 22 and an operating device 24. A control device 6 is provided, which is configured for controlling the various functions of the medical apparatus 2. In this, the control device 6 is preferably realized in the form of a CPU, which is configured by means of suitable software programs to control and execute the various functions.

Furthermore, in the medical apparatus 2 a communication device 3 is provided, which can both emit signals and receive signals. The communication device 3 is connected to the control device 6, from which it can be accessed. The control device 6 and/or the communication device 3 are configured to emit a wireless interrogation signal.

The treatment system 1 further comprises an identification device 4, which in the example shown schematically in FIG. 1 is carried on the belt of an operator 100, thus enabling the operator 100 to carry it with him or her without difficulty.

The operator 100 of the medical apparatus 2 is usually a dialysis nurse or other healthcare worker, who is trained to use the applicable medical apparatus 2, and accordingly authorized to operate the medical apparatus 2.

Since different types of medical apparatus 2 are usually available in a clinical facility or dialysis station, it may be necessary to allow only those operators 100 who have received training especially for that particular type to have access to a medical apparatus 2, or manipulate certain of its parameters, or operate it to the full extent.

Furthermore, the safety of treatment for the patients who are treated is increased if none but qualified operators 100 are permitted to operate the medical apparatus 2, and there is no possibility of operation by the patient himself, or by visitors or other persons who may be present in the clinical facility or dialysis station. This also avoids unintentional operation by visitors or other persons who may perhaps accidentally knock against the medical apparatus 2.

Accordingly, the medical apparatus 2 is provided with the communication device 3, which—for example in combination with the control device 6—is configured to emit periodically a wireless interrogation signal, for example in the form of a code word, in which case the communication device 3 operates with a low transmission power, for example a transmission power in the milliwatt range. When an operator 100 carrying a corresponding identification device 4 is in the immediate vicinity of the medical apparatus 2, a communication device 40 provided in the identification device 4 can receive this wireless interrogation signal. The identification device 4 is accordingly configured to receive the wireless interrogation signal. Correspondingly, the communication device 3 and the identification device 4 are configured to communicate using the same signal type, hence for example in the same frequency band using the same communication protocol. As a response to the interrogation signal, the communication device 40 is configured to send from the identification device 4 a suitable wireless identification signal, for example a code word. This code word is received by the communication device 3 in the medical apparatus 2, and appropriately evaluated.

Each identification device 4 used in a clinical facility or dialysis station is allocated, for example, an individual code word. It is particularly preferable if each individual operator 100 is allocated his or her own code word. In this manner the identification of the operator can be carried out, either by allocation of the identification device 4 to the corresponding operator 100 in a particular work shift, or else by the unique allocation of the code word to the operator 100.

Due to the low transmission power used by the communication device 3 when emitting the interrogation signal, only those identification devices 4 that are within a small radius of the communication device 3 are interrogated. This radius is, for example, the distance R1 of approximately 1 m to 5 m, preferably one meter, shown in FIG. 2.

Accordingly, if an operator 100 is in the immediate vicinity, for example within a radius R1 of 1 m-5 m around the medical apparatus 2, medical apparatus 2 can recognize precisely which operator is present from the identification signal emitted by the identification device 4 and received by the communication device 3.

The control of the medical apparatus 3 for carrying out the above-mentioned identification of an operator 100 is preferably accomplished by a computer program product running in the control device 6 of the medical apparatus 3. The medical apparatus 2 can preferably carry out a comparison with an authorization database 5, which either is directly connected with the communication device 3 or the control device 6, and accordingly located within the medical apparatus 2, or else is accessible via an external network.

The medical apparatus 2 accordingly queries the authorization database 5 on the basis of the identification signal received from the identification device 4, and can thereby determine whether the operator 100, to whom the applicable identification signal is allocated, is authorized to use this particular medical apparatus 2 or not. If the operator 100 is authorized, he or she can carry out all the operating steps or parameter changes available to him or her, for example via the operating unit 24 on the medical apparatus 2.

If the medical apparatus 2 determines when querying the operator authorizations in the authorization database 5 that the operator 100 is not authorized to operate the medical apparatus 2, the applicable operator either cannot change any parameter, or can change only selected parameters of the medical apparatus 2. The operating options are correspondingly locked for the unauthorized operator.

In a further preferred variant, differing levels of authorization are allocated in the authorization database 5. For example a doctor, whose identification device 4 transmits a particular identification signal to the communication device 3, can be given full access via the authorization database 5 to the medical apparatus 2. A fully trained and appropriately certified dialysis nurse can similarly receive full access to the medical apparatus 2. On the other hand, auxiliary staff can receive only restricted access, for example only to selected parameters of the medical apparatus 2. At the same time, the medical apparatus 2 can be configured such that operation of medical apparatus 2 via the operating device 24 is impossible without the sending of a valid identification signal. In one variant, some parameters are generally accessible, but those which are critical to the treatment and/or to patient safety are reserved for identified and authorized operators only.

All parameter changes that are performed, and/or all operating steps carried out on the medical apparatus 2, are logged in a log database 26. In this context, a log is kept not only of the actual operating steps and the time of performance of these operating steps, but also of which operator 100 and/or which operators are identified in the immediate vicinity of the medical apparatus 2, in order by this means to achieve a direct attribution of operating steps to the applicable operators. In this manner a treatment can be logged or documented still more completely.

In a preferred and particularly efficient manner of operation, the operator 100 carries the identification device 4 for example in the form of a wristwatch. If the operator 100 is in the vicinity of the medical apparatus 2, the communication device 40 in the identification device 4 receives the signal periodically emitted by the communication device 3 of the medical apparatus 2, which wakes the microprocessor in the identification device 4 from a sleep mode and causes it to respond with the code word, using in this case too a very low transmission power. After sending the applicable code word, the microprocessor returns to sleep mode. In this manner a highly energy-efficient operation of the identification device 4 can be achieved, with the result that an autonomous energy supply for the identification device 4, for example using an accumulator or a battery 44, either has a particularly long lifetime or can be small enough to achieve a high degree of carrying or wearing comfort for the identification device 4.

The identification device 4 can also be realized by a computer program product running on a mobile phone, smartphone and/or portable computer, in particular a tablet PC, with the computer program product thereby acting on the components of the said device such that the device is configured to enable the reception of the interrogation signal from the communication device 3 of the medical apparatus 3 and also transmission of the identification signal in response to the interrogation signal.

Figure 3:
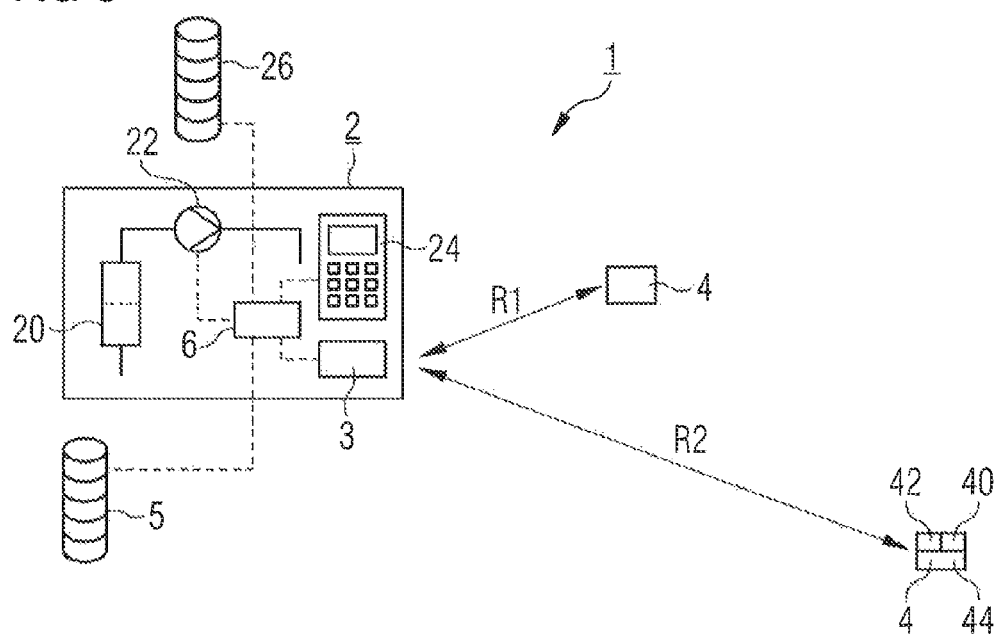
FIG. 3 a schematic diagram of the medical apparatus and an identification device at two different distances.

In a particularly preferable variant, which is also shown in FIG. 3, the transmission power of the communication device 3 of the medical apparatus 2 is greatly increased compared to its normal operation if an alarm is triggered. Here, for example, transmission powers in the milliwatt range, for example 2 milliwatts, can be used in order to impart an alarm signal to identification devices 4 which are located within a wider radius, for example the radius R2 of, for example, 20 m around the medical apparatus 2. In this case it is particularly preferable for the identification device 4 to have, along with the communication device 40, also an alerting device 42, which can for example emit an acoustic alarm and/or an optical alarm. In a particularly preferred variant, not only the actual alarm is transmitted, but also the location of the medical apparatus 2 that issues the alarm as well as the reason for the alarm, for example the parameters that triggered the alarm. The operator 100 who receives the alarm can accordingly recognize immediately, based on the transmitted reason for the alarm, what medical situation is to be expected at the medical apparatus 2 that issued the alarm.

This alarm is normally triggered by a call system or nurse call system, already provided due to the established safety standards, which serves to alert the medical personnel if a critical state of the medical apparatus occurs. The alert described here using an alarm signal sent to the identification device 4 increases the redundancy of the systems and at the same time enables the transmission of additional information to the medical personnel.

The wireless communication between the communication device 3 in the medical apparatus 2 and the communication device 40 in the identification device 4 can be performed using known communication standards and known communication solutions. A reliable and cost-effective system can for example be set up using wireless radio protocols such as for example the ZigBee standard. Other wireless radio protocols can of course also be envisaged, such as WLAN, Bluetooth or other conventional wireless radio protocols.

In an alternative embodiment, the identification device 4 can also be realized in passive form, and enable user identification via an RFID chip. Such a variant enables the identification device 4 to operate without a power supply. An RFID chip can for example also be incorporated in an operator's name badge.

Furthermore, an infra-red connection can be established between the identification device 4 and the communication device 3 of the medical apparatus 2, preferably serving as an addition to the wireless radio connection as a secure means of identification of the operator 100 during operation of the operating unit 24. The establishment of an infra-red connection can also serve as an additional safety measure when multiple operators are identified in the vicinity of the medical apparatus 2, in order to identify which operator is actually making adjustments to the medical apparatus 2. This exploits the fact that the infra-red connection can be established only if there is a line-of-sight connection. Thus if there are other identified operators in the vicinity of the medical apparatus 2, who may for example be operating a neighboring medical apparatus but are also identified by the medical apparatus in question, these operators are not facing towards the medical apparatus in question and cannot therefore establish an infra-red connection. This enables a more exact allocation of the operators.

As already described, the emission of signals via the communication device 3 from the medical apparatus 2, in order to inquire what identification devices 4 are in the immediate vicinity, can either be performed periodically, or else it can be initiated each time actual operation using the operating unit 24 is to take place. In the latter manner, the pollution of the area with potentially disruptive signals can be further reduced.

In a preferred variant, the identification device 4 can also be configured to emit a wireless identification signal periodically. This is preferably done using a low transmission power. In this manner it becomes possible to notify the available medical apparatuses 2 of the presence of a particular identification device 4, and hence of a particular operator. Such a notification can for example then cause the medical apparatus 2 to transmit a particular piece of information to the identification device 4. As one example, the identification device 4 of a member of the maintenance staff can periodically emit an identification signal which is then received by a medical apparatus 2. If, prior to this, a need for maintenance of the medical apparatus 2 has been determined, for example by means of its control device 6, the medical apparatus 2 can use its communication device 3 to send a suitable alert, or suitable information, to the maintenance staff member's identification device 4. Accordingly, maintenance can now for example be carried out immediately, or the maintenance staff member can immediately determine what maintenance will be required.

To the extent that this is applicable, all individual features described in the individual example embodiments can be combined with each other and/or exchanged, without departing from the field of the invention.

LIST OF REFERENCE SIGNS 1 treatment system
100 operator
101 arterial blood line
102 blood pump
103 dialysis filter
104 venous line
105 dlalysate line
106 dialysate line
107 touch screen
108 control device
110 medical apparatus according to the state of the art
2 medical apparatus
4 filter
22 peristaltic pump
24 operating unit
26 log database
3 communication device
4 identification device
40 communication device
42 alerting device
44 battery
5 authorization database
6 control device
R1 small distance
R2 large distance

The invention claimed is:

1. A treatment system for a patient for performing a dialysis treatment comprising:
   a dialysis apparatus having a communication device which is configured to emit a wireless interrogation signal and receive a wireless identification signal; and
   an identification device that can be carried by an operator, said identification device configured to send a wireless identification signal to the dialysis apparatus, to emit an identification signal at least one of periodically and after reception of an interrogation signal from the communication device of the dialysis apparatus, and to receive and display information sent by the communication device, wherein the communication device is configured to verify whether the identification signal belongs to a member of the maintenance staff and, when the identification signal is an identification signal of a member of the maintenance staff and when a need for maintenance of the dialysis apparatus has been determined, to send at least one of a suitable alarm and suitable information to the identification device of the maintenance staff member regarding the need for maintenance, said maintenance staff member, in response to said at least one of an alarm and information, then acting to do at least one of determine what maintenance of the dialysis apparatus is required, and perform the required maintenance.

2. The treatment system according to claim 1, wherein the communication device of the dialysis apparatus and the identification device are configured to communicate with each other via a common wireless radio standard.

3. The treatment system according to claim 1, wherein the communication device of the dialysis apparatus and the identification device are configured to communicate with each other via an infra-red signal.

4. The treatment system according to claim 1, wherein a log database is provided and the dialysis apparatus is configured to enter operating accesses and the identities of the operators who effect the operating accesses into the log database.

5. The treatment system according to claim 1, wherein the identification device is formed as a watch, a pager, a mobile phone, or a portable computer.

6. The treatment system according to claim 1, wherein the identification device is formed as a tablet PC.

7. A method for identifying an operator of a medical apparatus for a treatment system, the medical apparatus having a communication device which is configured to emit a wireless interrogation signal and receive a wireless identification signal and an identification device that can be carried by an operator, said method comprising the steps of:
wirelessly emitting an interrogation signal by the communication device of the medical apparatus to at least one identification device carried by an operator, the identification device identifying the operator;
sending a wireless identification signal from the identification device to the medical apparatus in response to receipt of the interrogation signal;
receiving, in the communication device of the medical apparatus, the wireless identification signal sent by the identification device in response to the interrogation signal received from the medical apparatus;
identifying, by the medical apparatus, the operator based on the wireless identification signal received from the identification device and verifying whether the identification signal belongs to a member of the maintenance staff; and
when the identification signal is an identification signal of a member of the maintenance staff and when a need for maintenance of the medical apparatus has been determined, said communication device sending at least one of an alarm and information to the identification device of said maintenance staff member on which said information is displayed; and
said maintenance staff member, in response to said at least one of an alarm and information, then acting to do at least one of determine what maintenance of the medical apparatus is required, and perform the required maintenance.

8. The method according to claim 7, wherein the identification device is formed as a watch, a pager, a mobile phone, or a portable computer.

9. The method according to claim 7, wherein the identification device is formed as a tablet PC.

10. The method according to claim 7, wherein the identification device is formed as a watch.

11. A dialysis apparatus for use in a dialysis treatment system comprising:
a communication device associated with said dialysis apparatus and configured to emit a wireless interrogation signal and receive a wireless identification signal; and
said dialysis treatment system including an identification device that can be carried by an operator, said identification device configured to send a wireless identification signal to the communication device of the dialysis apparatus, to emit an identification signal at least one of periodically and after reception of an interrogation signal from the communication device of the dialysis apparatus, and to receive and display information sent by the communication device of the dialysis apparatus, wherein the communication device is configured to verify whether the identification signal belongs to a member of the maintenance staff and, when the identification signal is an identification signal of a member of the maintenance staff and when a need for maintenance of the dialysis apparatus has been determined, to send at least one of a suitable alarm and suitable information to the identification device on which this information is displayed, said maintenance staff member, in response to said at least one of an alarm and information, then acting to do at least one of determine what maintenance of the dialysis apparatus is required, and perform the required maintenance.

12. The dialysis apparatus according to claim 11, wherein the communication device of the dialysis apparatus and the identification device are configured to communicate with each other via a common wireless radio standard.

13. The dialysis apparatus according to claim 11, wherein the communication device of the dialysis apparatus and the identification device are configured to communicate with each other via an infra-red signal.

14. The dialysis apparatus according to claim 11, wherein a log database is provided and the dialysis apparatus is configured to enter operating accesses and the identities of the operators who effect the operating accesses into the log database.

15. The dialysis apparatus according to claim 11, wherein the identification device is formed as a watch, a pager, a mobile phone, or a portable computer.

16. The dialysis apparatus according to claim 11, wherein the identification device is formed as a tablet PC.

* * * * *